(12) United States Patent
Van Orden et al.

(10) Patent No.: US 6,346,887 B1
(45) Date of Patent: Feb. 12, 2002

(54) EYE ACTIVITY MONITOR

(75) Inventors: Karl F. Van Orden, San Diego; Scott Makeig, Cardiff; Tzyy-Ping Jung, San Diego, all of CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/408,653

(22) Filed: Sep. 14, 1999

(51) Int. Cl.[7] .............................................. G08B 23/00
(52) U.S. Cl. ........................ 340/575; 180/272; 340/576
(58) Field of Search .................. 340/575, 576; 180/272

(56) References Cited

U.S. PATENT DOCUMENTS 5,649,061 A * 7/1997 Smyth .......................... 706/16
6,092,058 A * 7/2000 Smyth .......................... 706/10
6,097,295 A * 8/2000 Griesinger et al. ......... 340/576

* cited by examiner

*Primary Examiner*—Thomas Mullen
(74) *Attorney, Agent, or Firm*—Harvey Fendelman; James A. Ward; Eric James Whitesell

(57) ABSTRACT

An eye activity monitor of the present invention integrates multiple eye activity parameters and applies them to alertness models to determine the onset of operator fatigue or drowsiness in real time.

4 Claims, 1 Drawing Sheet

EYE ACTIVITY MONITOR

LICENSING INFORMATION

The invention described below is assigned to the United States Government and is available for licensing commercially. Technical and licensing inquiries may be directed to Harvey Fendelman, Patent Counsel, Space and Naval Warfare Systems Center San Diego, Code D0012 Rm 103, 53510 Silvergate Ave., San Diego, Calif. 92152; telephone no. (619) 553-3001; fax no. (619) 553-3821.

BACKGROUND OF THE INVENTION

The present invention relates generally to alertness monitoring systems for detecting operator fatigue. More specifically, but without limitation thereto, the present invention relates to a device for monitoring eye activity to detect the onset of low alertness levels.

Loss of alertness associated with cognitive fatigue or boredom is an administrative and a safety concern for any system that requires sustained observation by a human operator. Monitoring human operators for signs of fatigue is important in transportation, security, and process control environments where lapses in attention may be disastrous. Methods for alertness monitoring have been proposed based on measures of operator actions, electro-encephalographic (EEG) activity, and measures of eye activity. Several eye activity parameters have been shown to be sensitive to drowsiness or to time on task, which is linked indirectly to the onset of drowsiness in monotonous task environments. For example, using electro-oculographic (EOG) techniques, it has been reported that blink duration and blink rate typically increase while blink amplitude decreases as a function of cumulative time on task. Other EOG studies have found that saccade, i.e. movements of the eye from one fixation point to another, frequencies and velocities decline as time on task increases.

Other recent studies have reported on eye activity relative to performance level in simulated transportation environments. Morris and Miller demonstrated in 1996 the sensitivity of EOG measures to fatigue in aircraft pilots during a 4 ½-hour flight. Weirwille, Wreggit, and Knipling reported in 1994 that a measure of eyelid droop, i.e. the percentage of time that the eyelid covers 80 percent or more of the pupil, may be a useful component of eye activity to detect drowsiness during simulated driving tasks. Using video analysis techniques, other investigators have shown that pupil diameter increases as a function of drowsiness (Lowenstein and Lowenfeld, 1962; Yoss, Moyer, and Hollenhorst, 1970).

A disadvantage of the methods mentioned above is that they are generally obtrusive and require direct physical contact with the subject. Another disadvantage of these methods is that they require integration over several minutes, which rules out estimation of drowsiness in real time. A need therefore exists for a non-obtrusive eye activity monitor that does not require a mechanical or electrical connection to the subject and that can estimate drowsiness in real time.

SUMMARY OF THE INVENTION

The present invention is directed to overcoming the problems described above, and may provide further related advantages. No embodiment of the present invention described herein shall preclude other embodiments or advantages that may exist or become obvious to those skilled in the art.

An eye activity monitor of the present invention integrates multiple eye activity measures and applies them to general or custom alertness models to determine the onset of operator drowsiness in real time.

An advantage of the eye activity monitor of the present invention is that no physical contact with the subject is required.

Another advantage is that eye activity measurements may be made in a non-obtrusive manner, avoiding distractions that might impair the performance of the subject.

The features and advantages summarized above in addition to other aspects of the present invention will become more apparent from the description, presented in conjunction with the following drawings.

DESCRIPTION OF THE INVENTION

Figure 1:
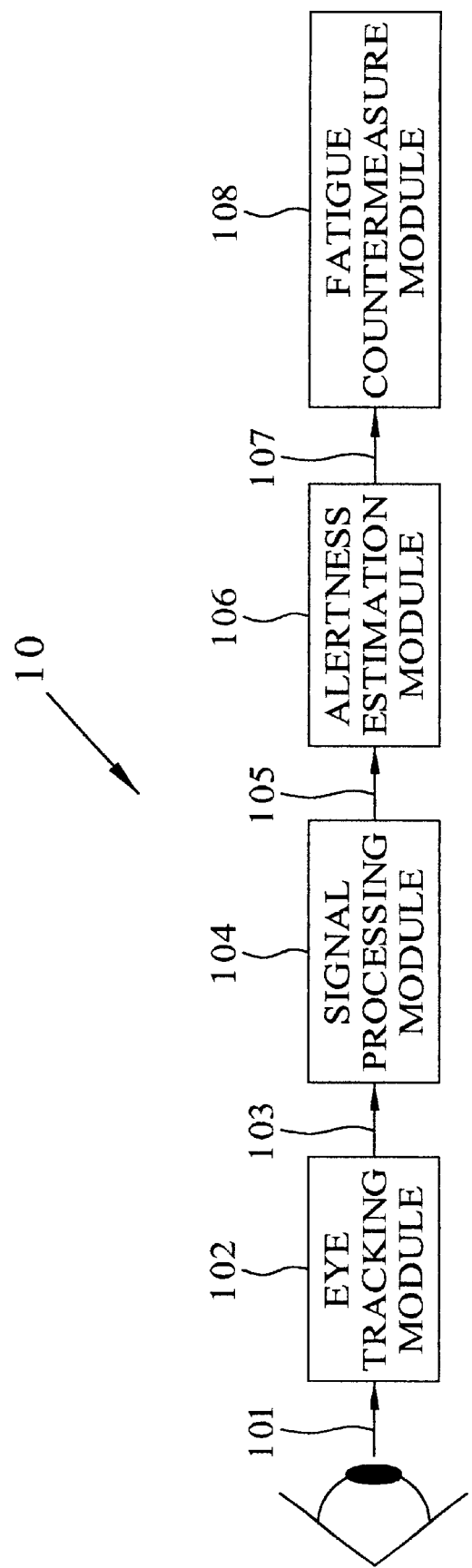
FIG. 1 is a functional diagram of an eye alertness monitor of the present invention.

The following description is presented solely for the purpose of disclosing how the present invention may be made and used. The scope of the invention is defined by the claims.

FIG. 1 is a functional diagram of an eye alertness monitor 10 of the present invention. An eye tracking module 102 accepts an optical input 101 from which module 102 measures eye position and pupil diameter. A commercial video-based eye tracking system or any technology that can output horizontal and lateral eye position and pupil diameter data at a rate of at least 60 Hz may be used for eye tracking module 102. Examples of commercially available eye tracking systems are the Applied Science Laboratory Model 4000 and the SensoriMotor Eyelink system. A video-based eye tracking system may be constructed using miniature cameras with video processing hardware and software, for example, National Instruments Labview video processing equipment. A gimbaled camera designed to follow the eyes as the face is moved may be mounted on the operator console, vehicle dashboard, or other object being observed below the subject's normal line of sight.

Eye position and pupil diameter data 103 from eye tracking module 102 is input at a refresh rate preferably at least 60 times a second to signal processing module 104. Signal processing module 104 may be for example, a desktop computer or a microprocessor circuit for performing the following functions: retaining a sample history of eye position and pupil diameter data 103; calculating a baseline pupil diameter from the pupil diameter data; detecting a reduction in pupil diameter from the baseline value (a sign of eyelid droop); calculating blink frequency and duration; calculating visual fixation activity; and updating the mean pupil diameter value.

The sample history is retained for calculating a moving average of the pupil diameter, and preferably contains at least the previous 90 seconds of eye position and pupil diameter data 103. The baseline value of the pupil diameter may be calculated during an initial period of from one to three minutes at the beginning of a monitoring cycle by summing and averaging non-zero (non-blink) pupil diameter values.

A reduction in the baseline pupil diameter of 35–50% for more than two seconds may be an indication of severe eyelid droop, and intervention may be required to restore the subject's attention. Eyelid droop this severe may nearly cover the entire pupil during conditions of extreme drowsiness without excessive blinking or complete closure of the eye. Comparing the pupil diameter to a threshold of 35–50% of the baseline value ensures that severe eyelid droop will be detected and counted as a blink if sufficiently brief or as a loss of pupil diameter measurement signal indicating the onset of sleep or malfunction of eye tracking module 102. Moving averages of pupil diameter are calculated preferably over a 40–60 second time period and updated about every 10 seconds.

Blinking is detected from the pupil diameter data by identifying a reduction in pupil diameter of 35–50% or more from the baseline value. A blink may be defined as a partial or complete eye closure lasting 83 milliseconds or more. The 83 millisecond threshold avoids false blink counts due to transient signal losses from light reflections off the skin and from system noise generated by eye tracking module 102. Blink duration is defined as the time interval between blink onset and the return of pupil diameter to greater than 35% of the baseline value. Blink duration and frequency are calculated preferably over a 60 second period and updated at least every 10 seconds.

Eye position and pupil diameter data 103 also contains the x-y coordinates of the pupil center to measure visual fixation. The x-y coordinates are updated preferably at least 60 times a second and are used to calculate the location and duration of visual fixations. It is believed that visual fixations on points-of-regard are psychologically significant clusters indicating spatial locations where visual information is being integrated for processing by higher brain centers. Visual fixations are calculated using one or more well-known space-by-time boundary algorithms. These algorithms compute a moving mean centroid of points-of-regard as well as a moving estimate of variance in distance of the points-of-regard from the centroid. Such algorithms may include steps to determine when one visual fixation has terminated and a new visual fixation has begun. Typically, a new fixation centroid is determined when several consecutive points-of-regard deviate from a current fixation centroid by a distance that exceeds the running estimate of variance of points around the current fixation centroid plus some threshold distance or visual angle. From these visual fixation activity algorithms, estimates of visual fixation frequency, i.e. fixations per minute, and total visual fixation duration are derived for a period of, for example, 20–60 seconds. Visually demanding tasks such as air traffic control may use smaller time periods, for example, 20–30 seconds, while simpler monitoring tasks may use larger time periods.

The above five calculations of eye activity, i.e. pupil diameter, blink frequency, blink duration, visual fixation frequency, and visual fixation duration, are made from the most recent 30–60 second period and updated preferably at least every 10 seconds. These calculations are output as eye activity data 105 to alertness estimation module 106.

Alertness estimation module 106 integrates eye activity data 105 and generates an estimate of drowsiness. The drowsiness estimate may be based on a common equation for all operators, or the equation may be individually derived for each operator by correlating current eye activity data with eye activity data taken during calibration tasks designed to induce drowsiness. The individual approach is more sensitive to variation of eye activity parameters from one individual to another, however it usually requires training of a regression or neural net model for each operator.

A general regression model may be based upon summing visual fixation frequency and duration changes from numerous subjects. An exemplary formula for estimating drowsiness is: tracking error (for example, lane drift of a moving vehicle)=−0.77*fixation duration+0.21*fixation frequency. This model may be appropriate for vehicular operation, although verification of the model parameters is recommended using a simulator or actual operational tests. The model parameters may be revised for tasks requiring a greater degree of visual scanning behavior, for example, air traffic control and sonar.

Specific regression models may outperform general models because of individual variability in changes in eye activity as a function of drowsiness. Specific models may be based on eye activity data taken while an operator performs a task that is identical to or highly similar to the monitoring task under both alert and drowsy conditions. The drowsiness state during this data acquisition should be sufficiently severe to have a deleterious effect on task performance. The eye activity data may then be used to derive a regression model or to train an artificial neural network. Preferably, multiple data acquisition sessions should be recorded to optimize the model's effectiveness.

Problems with multi-colinearity, i.e, when several eye activity measures correlate with the variable of interest (tracking error in this case) and also with each other, may complicate the development of individual regression models. In this case one of the variables should be ignored to develop a more reliable regression equation. Also, these models may not work well under conditions that differ from the sessions used to derive the training data set. Extra care is needed to ensure that the regression model is robust over time yet sufficiently sensitive to changes in alertness.

Alternatively, an artificial neural network may be trained on experimentally derived data to produce a specific model of eye activity changes with alertness. An exemplary neural network for analyzing eye activity data and deriving an estimate of alertness is a feedforward three-layer (one hidden layer) neural network trained by back-propagation. Care should be taken to ensure that the neural net is not overtrained on a given data set of task and eye activity measurements, otherwise the model may not generalize well to different conditions and tasks. One method of preventing overtraining uses several neural nets with different initial weights on the same subset of test data and selecting the neural net that produces the best correlation between estimated to actual performance. For maximum sensitivity, this neural net should be trained for each operator while they are performing the actual task or a comparable simulation. For example, a compensatory tracking task or a driving simulator may provide adequate weight training data, provided that any error associated with the training task may be correlated to error associated with the actual task.

As part of an automobile alertness monitoring system, the neural network could learn to associate eye activity patterns with various levels of driving performance assessed by a parallel onboard system logging performance measures collected while driving in areas equipped with an intelligent highway vehicle system (IHVS). Eye activity parameters could then be used to refine real-time estimates of driving characteristics, such as lane drift, while driving in areas with or without IHVS. Thresholds could be established by the alertness monitoring system and the driver for activating alerting signals or other fatigue countermeasures. Other tasks, such as air traffic and process control, may require training tasks and simulations containing scanning parameters similar to the actual tasks.

An estimated alertness score 107 is input from alertness estimation module 106 to countermeasures module 108 to determine whether and what kind of alerts are generated. Thresholds for countermeasure alerts may be set appropriately for each application, and may consist of alarms to the operator or to the operator's supervisor. For process control systems, alarms may be transmitted to a process monitoring system.

Other modifications, variations, and applications of the present invention may be made in accordance with the above teachings other than as specifically described to practice the invention within the scope of the following claims.

We claim:

1. An eye activity monitor for alerting a task operator, the monitor comprising:
   a signal processing module comprising
      input means for receiving eye activity data representing the eye activity of the task operator,
      an eye tracking module coupled to the input means for measuring the eye activity of the task operator and for producing a signal representing the eye activity data including pupil diameter and pupil position,
      update means for updating the eye activity data at least 60 times per second,
      memory means for storing a sample history representing at least ninety seconds of the eye activity data,
      processing means for calculating eye activity parameters representing a moving average of pupil diameter, a history of blink frequency and duration, and a history of visual fixation frequency and duration, and
      output means for producing a signal representing the calculated eye activity parameters for use in generating an alertness estimate; and
   a fatigue countermeasures module for generating alarms to alert the task operator responsive to the alertness estimate.

2. An eye activity monitor for alerting a task operator, the monitor comprising:
   a signal processing module comprising
      input means for receiving eye activity data representing the eye activity of the task operator,
      memory means for storing a sample history representing at least ninety seconds of the eye activity data,
      processing means for calculating eye activity parameters representing a moving average of pupil diameter, a history of blink frequency and duration, and a history of visual fixation frequency and duration,
      update means for updating the calculated eye activity parameters at least once every ten seconds, and
      output means for producing a signal representing the calculated eye activity parameters for use in generating an alertness estimate; and
   a fatigue countermeasures module for generating alarms to alert the task operator responsive to the alertness estimate.

3. An eye activity monitor for alerting a task operator, the monitor comprising:
   a signal processing module comprising
      input means for receiving eye activity data representing the eye activity of the task operator,
      memory means for storing a sample history representing at least ninety seconds of the eye activity data,
      processing means for calculating eye activity parameters representing a moving average of pupil diameter, a history of blink frequency and duration, and a history of visual fixation frequency and duration, and
      output means for producing a signal representing the calculated eye activity parameters for use in generating an alertness estimate;
      an alertness estimation module coupled to the output means for accepting the calculated eye activity parameters and for producing an alertness estimate corresponding to an alertness function comprising a linear regression model; and
   a fatigue countermeasures module for generating alarms to alert the task operator responsive to the alertness estimate.

4. The eye activity monitor of claim 3 wherein the alertness estimation module further comprises:
   estimation function means for generating a signal representing the alertness estimate corresponding to an alertness function $A*Vfd+B*Vff$, where A and B are preselected coefficients, Vfd is a calculated eye activity parameter representing visual fixation duration, and Vff is a calculated eye activity parameter representing visual fixation frequency.

* * * * *